(12) United States Patent
Noh et al.

(10) Patent No.: US 7,011,961 B2
(45) Date of Patent: Mar. 14, 2006

(54) METHOD FOR L-THREONINE PRODUCTION

(75) Inventors: Kap-Soo Noh, Seoul (KR); Yeong-Chul Kim, Seoul (KR); Jae-Yong Park, Seoul (KR); Dai-Chul Kim, Kyungki-do (KR); Jin-Ho Lee, Kyungki-do (KR); Seung-Han Ok, Busan (KR)

(73) Assignee: Cheil Jedang Corporation (KR)

( * ) Notice: Subject to any disclaimer, the term of this patent is extended or adjusted under 35 U.S.C. 154(b) by 173 days.

(21) Appl. No.: 10/257,465

(22) PCT Filed: Feb. 14, 2002

(86) PCT No.: PCT/KR02/00230

§ 371 (c)(1),
(2), (4) Date: Oct. 11, 2002

(87) PCT Pub. No.: WO02/064808

PCT Pub. Date: Aug. 22, 2002

(65) Prior Publication Data

US 2003/0153057 A1 Aug. 14, 2003

(30) Foreign Application Priority Data

Feb. 13, 2001 (KR) .......................... 2001-6976

(51) Int. Cl.
*C12P 13/08* (2006.01)
*C12P 9/88* (2006.01)
*C12N 1/20* (2006.01)
*C12N 15/74* (2006.01)
*C07H 21/04* (2006.01)

(52) U.S. Cl. ................ 435/115; 435/106; 435/183; 435/232; 435/252.1; 435/252.3; 435/252.33; 435/320.1; 536/23.1; 536/23.2

(58) Field of Classification Search ................ 435/106, 435/115, 183, 232, 252.1, 252.3, 252.33, 435/320.1, 119; 536/23.1, 23.2
See application file for complete search history.

(56) References Cited

U.S. PATENT DOCUMENTS

| 5,538,873 A | 7/1996 | Debabov et al. ............ 435/115 |
| 5,939,307 A | 8/1999 | Wang et al. | |

FOREIGN PATENT DOCUMENTS

| JP | 2-219582 | 9/1990 |
| KR | 1992-0008365 | 9/1992 |
| KR | 1994-0014793 | 7/1994 |
| WO | WO 2001-27258 | 4/2001 |

OTHER PUBLICATIONS

Herman, T. J Biotechnol. Sep. 4, 2003;104(1–3):155–72.*

"pBRINT-Ts: a plasmid family with a temperature-sensitive replicon, designed for chromosomal integration into the lacZ gene of *Escherichia coli*"; Authors: Sylvie Le Borgne, Beatriz Palmeros, Fernando Valle, Francisco Bollvar and Guillermo Gosset; Elsevier; Gene An International Journal on Genes and Genomes, vol. 223; 1998; pp. 213–219.

"L–Threonine production by L–aspartate– and L–homoserine–resistant mutant of *Escherichia coli*"; Authors: Satoru Furukawa, Akio Ozaki and Toshihide Nakanishi; Applied Microbiology and Biotechnology, vol. 29; 1988; pp. 550–553.

* cited by examiner

*Primary Examiner*—Ponnathapu Achutamurthy
*Assistant Examiner*—Christian L. Fronda
(74) *Attorney, Agent, or Firm*—Cantor Colburn LLP

(57) ABSTRACT

A method of producing L-threonine using a microorganism is provided, one or more copies of each of the phosphoenolpyruvate carboxylase gene and the threonine operon are additionally intedgrated into a particular site of the chromosomal DNA of the microorganism, whiel its inherent phophoenolpyruvate carboxylase gene and threonine operon remain.

2 Claims, 2 Drawing Sheets

SEQUENCE LISTING

<160> NUMBER OF SEQ ID NOS: 2

<210> SEQ ID NO 1
<211> LENGTH: 29
<212> TYPE: DNA
<213> ORGANISM: Artificial
<220> FEATURE:
<223> OTHER INFORMATION: primer

<400> SEQUENCE: 1
aggaattctt ccgcagcatt tgacgtcac                29

<210> SEQ ID NO 2
<211> LENGTH: 30
<212> TYPE: DNA
<213> ORGANISM: Artificial
<220> FEATURE:
<223> OTHER INFORMATION: primer -continued

<400> SEQUENCE: 2
aggaagcttt tagccggtat tacgcatacc                30

METHOD FOR L-THREONINE PRODUCTION

BACKGROUND OF INVENTION

1. Field of Invention

The present invention relates to the production of L-threonine involving microorganisms. More particularly, the present invention relates to a process for producing L-threonine with a high yield, in which additional one or more copies of the phosphoenolpyruvate carboxylase (ppc) gene and the threonine operon are inserted into a particular site of the chromosomal DNA of a microorganism, while its inherent ppc gene and threonine operon remain, to increase the expression of the ppc gene encoding an enzyme to convert phosphoenol pyrvate to oxaloacetate, which is a threonine biosynthetic precursor, and the expression of genes encoding enzymes engaged in the synthetic pathway of threonine from oxaloacetate, such as aspartokinasel-homoserine dehydrogenase (thrA), homoserine kinase (thrB), and threonine synthase (thrC).

2. Description of Related Art

L-threonine, a kind of essential amino acid, is widely used as an additive to animal fodder and food, and as fluids and synthetic materials for medical and pharmaceutical use. L-threonine is produced by fermentation using synthetic mutants derived from wild types of *Escherichia Coli, Corynebacterium, Serratia,* and *Providencia.* These variant strains are known to include amino acid analogs, pharmaceutical-resistant mutants, and synthetic pharmaceutical-resistant mutants rendered auxotrophic for diaminopimelic acid, methionine, lysine, or isoleucine (Japanese Laid-open Patent Application No. hei 2-219582, *Appl., Microbiolo. Biotechnol.,* 29, 550–553 (1988), and Korean Patent Publication No. 92-8365).

A common approach to increase the level of expression of a particular gene uses a plasmid that gives a greater copy number to a microorganism in order to increase the number of genes in the microorganism (Sambrook et al., *Molecular cloning, Second Edition,* 1989, 1.3–1.5). A target gene is integrated into a plasmid, and the host microorganism is transformed with the recombinant plasmid to cause an increase in the number of genes in the host microorganism according to the copy number in the plasmid. A partial success in this type of approach to improve threonine productivity is reported in U.S. Pat. No. 5,538,873. However, most technologies using such recombinant plasmids overexpress a particular gene, which is undesirable for the host microorganism, and causes a problem of plasmid instability so that the plasmid is lost during cultivation of the recombinant strain.

To address this problem, approaches to add antibiotics to culture media or to use an expression regulatory plasmid were suggested (Sambrook et al. *Molecular cloning, Second Edition,* 1989, 1.5–1.6 & 1.9–1.11). In using the expression regulatory plasmid to yield a particular product, cell cultivation is performed under non-expression conditions in the growth stage to reduce a load to the host microorganism and temporary expression is induced after full growth of the microorganism. However, most expression regulatory plasmids target protein synthesis. Producing primary metabolites is closely associated with the growth of microorganisms, so it is difficult to increase the yield of the primary metabolites unless target genes are expressed in the growth stage. The production of threonine, a primary metabolite, is such a case.

As an effort to compensate for this drawback, a particular threonine biosynthetic gene was incorporated into a chromosomal DNA to produce threonine (U.S. Pat. No. 5,939,307). However, this approach replaces a chromosomal gene by an inducible promoter-substituted gene, which is hardly expected to markedly increase the expression of the threonine operon gene.

Therefore, unlike the conventional substitution method, the present inventors have inserted an additional ppc gene and threonine operon into a particular site (lacZ gene) of the chromosomal DNA while the original chromosomal gene of a host microorganism remains, and found that it provides dual effects as a result of the original chromosomal gene and the inserted ppc gene and threonine operon. Most current genetic engineering techniques applied to increase the yield of threonine are focused on the biosynthetic pathway, starting with oxaloacetate. However, the present invention involves also ppc, which is an oxaloacetate inducer enzyme acting in the preceding step, as well as the threonine biosynthetic enzymes to purposely guide the flow of carbons from phosphoenolpyruvate into the oxaloacetate synthetic pathway. The present invention also allows insertion of two or more copies of gene if necessary.

SUMMARY OF INVENTION

To solve the above-described problems, it is an object of the present invention to provide a high-yield L-threonine production method which eliminates problems of plasmid instability and microbial growth inhibition arising with recombinant plasmid bearing strains and at the same time increases the expression of the phosphoenolpyruvate carboxylase (ppc) gene and the threonine operon.

The object of the present invention is achieved by a method of producing L-threonine using a microorganism, one or more copies of each of the phosphoenolpyruvate carboxylase gene and the threonine operon are additionally integrated into a particular site of the chromosomal DNA of the microorganism, while its inherent phosphoenolpyruvate carboxylase gene and threonine operon remain.

According to the present invention, by incorporating two or more copies of the ppc gene and the threonine operon into the chromosomal DNA, the levels of expression of the ppc gene, which encodes an enzyme to convert phosphoenolpyruvate to a threonine synthetic precursor, oxaloacetate, and the genes, of enzymes engated in the threonine synthesis from oxaloacetate, such as thrA (aspartokinase 1-homoserine dehydrogenase), thrB (homoserine kinase), and thrC (threonine synthase).

According to the present invention, any microorganism capable of producing L-threonine, including *Escherichia Coli, Corynebacterium, Serratia*, and *Providencia* can be used, but *Eschenichia Coli* is more preferred.

It is preferable that the ppc gene and the threonine operon additionally inserted into the microorganism is derived from a microorganism (synthetic mutant) resistant to threonine analogs, lysine analogs, isoleucine analogs, and methionine analogs.

According to the present invention, the ppc gene and the threonine operon may be additionally inserted into any site of the chromosomal DNA, except for the original threonine operon, but preferably into the lacZ gene site.

In the L-threonine production method according to the present invention, it is preferable that a ppc gene obtained from the chromosome of a L-threonine producing *E. coli* strain, TF4076 (KFCC 10718), by polymerase chain reaction (PCR) and a threonine operon cloned from the same chromosome are inserted into the chromosome of the host *E. coli* strain TF4076.

1. Threonine Operon Amid Phosphoenolpyrlivate Carboxylase Gene

The threonine operon and phosphoenolpyruvate carboxylase (ppc) gene used were cloned from the chromosome of TF40756 (Accession Number; KFCC10718, Korean Patent Application No. 90-22965). This strain is anxotrophic for methionine and resistant to threonine analogs (AHV: α-amino-β-hydroxyvaleric acid), lysine analogs (AEC: S-(2-aminoethyl)-L-cysteine), isolcucine analogs (α-aminobutyric acid) and methionine analogs (ethionine).

2. Integration Vector pBRINT-TsGm, a plasmid vector for use in chromosomal integration, was used (Sylvie Le Beatriz et al., 1998, *pBRINT-Ts: A plasmid family with a temperature-sensitive replicon, designed for chromosomal integration into the lacZ gene of Escherichia coli.*, Gene., 223, pp. 213–219). This vector has temperature sensitivity; it integrates the cloned genes of a plasmide into a site of the lacZ gene of the chromosomal DNA when cultured at 37° C. whereas the remaining plasmids in the plasma are lost when the cultivation temperature is raised to 44° C.

3. Recombinant Vector

The ppc gene derived from the chromosome of TF4076 by polymerase chain reaction (PCR) and the threonine operon derived from a vector cloned with the threonine operon, pAT94 (Korean Patent Application No. 92-24732), were cloned into BamH I and EcoR I sites of pBRINT-TsGm to construct a recombinant plasmid vector pGmTN-PPC. Strain TF4076 was transformed with the recombinant plasmid vector and then cultivated at 37° C. to induce integration of the cloned ppc gene and threonine operon into the site of lacZ gene of the chromosomal DNA. Then, the cultivation was continued at 44° C. to get rid of the remaining plasmids in the host strain.

4. Screening Method

Colonies that are resistant to gentamycin and sensitive to carbenicillin, and looks white, not blue, in a solid medium containing X-gal and IPTG were visually screened for recombinant strains. This screening method is based on the principle that integration of the ppc gene and the threonine operon into the IacZ gene of the chromosomal DNA inactivates the lacZ gene to lose its ability to decompose the chromophore X-gal.

These selected recombinant strains were compared with the host strain for threonine productivity. As a result, the host strain produced 20 g/L of threonine in 48 hours whereas pGmTN-PPC (Accession Number: KCCM-10236), one of the recombinant strains with the ppc gene and the threonine operon integrated into the chromosomal DNA, shows a highest threonine productivity at 27.0 g/L with a yield of about 35% (see Example 4). The pGmTN-PPC strain produces 102 g/L of threonine through fermentation in a 5-L fermentor with a higher yield of 35.4% then the host strain (see Example 5).

DETAILED DESCRIPTION OF INVENTION

The present invention will be described in greater detail by means of the following examples. The following examples are for illustrative purposes and are not intended to limit the scope of the invention.

EXAMPLE 1

Cloning of Phosphoenolpyruvate Carboxylase Gene

Figure 1:
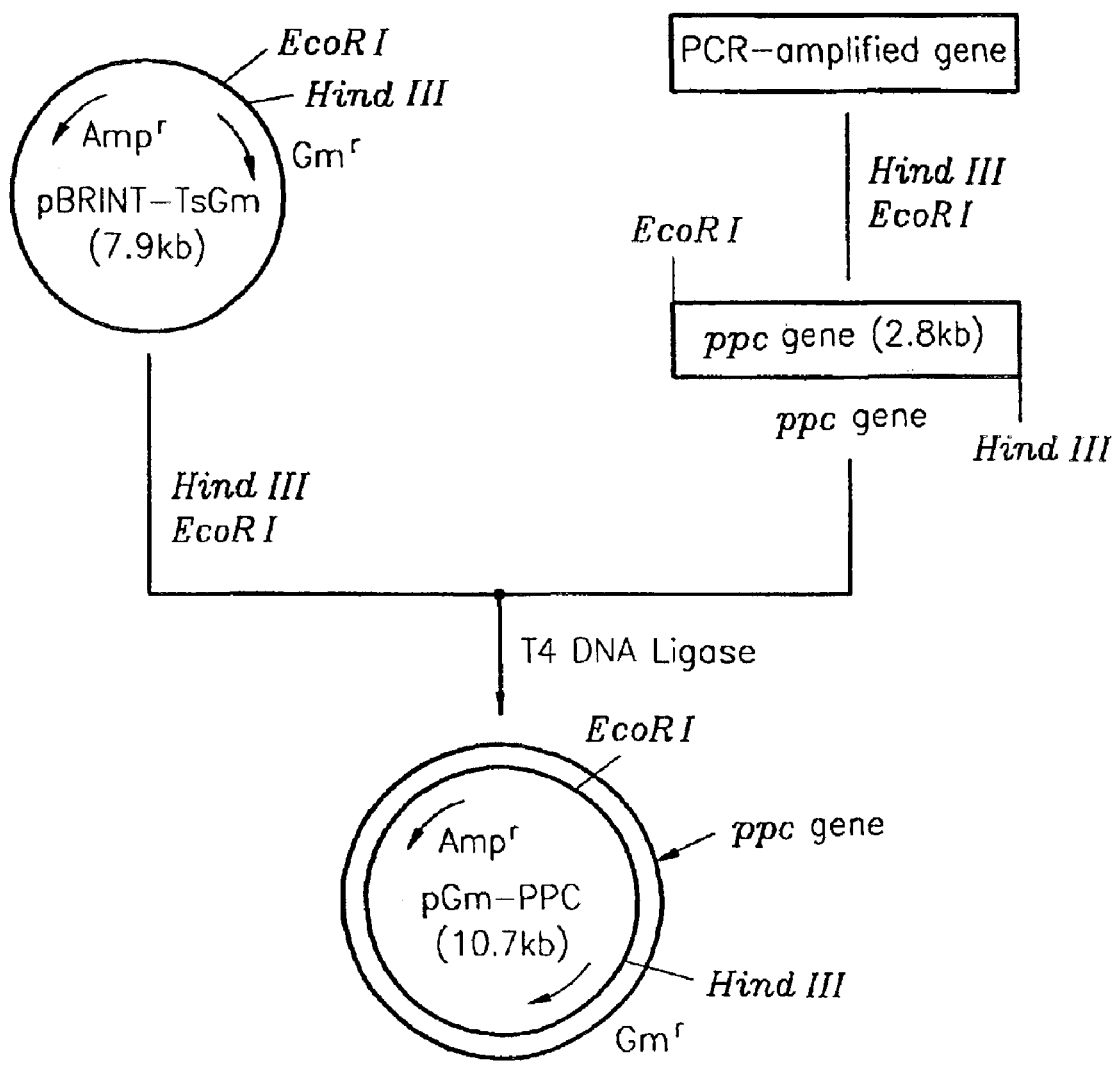
FIG. 1 depicts a process of cloning the phosphoenolpyruvate carboxylase (ppc) gene.

The process of cloning the phosphoenolpyruvate carboxylase (ppc) gene is illustrated in FIG. 1. The ppc gene was obtained from a threonine producing strain, TF 4076. Chromoromal DNA was isolated, digested with restriction enzyme Sal I, and subjected to electrophoresis to selectively isolate 4–5 kb DNA fragments. The ppc gene was amplified by using the isolated DNA fragments as templates and using primer 1 (5'-aggaattcttccgcagcatttgacgtcac-3') and primer 2 (5'-aggaagcttttagccggtattacgcatacc-3'). The amplified product was digested with EcoR I and Hind III and subjected again to electrophoresis to finally isolate a 2.8 kb ppc gene fragment. A 7.6 kb pBRINT-TsGm, a kind of pBRINT-Ts vectors, from the National University of Mexico was used for cloning (*Sylvie Le Beatriz et al., 1998, pBRINT-Ts: A plasmid family with a temperature-sensitive replicon, designed for chromosomal integration into the lacZ gene of Escherichia coli., Gene.*, 223, pp. 213–219). pBRINT-TsGm was double digested with the same restriction enzymes, EcoR I and Hind III, and ligated with the isolated ppc gene fragment by T4 DNA Ligase. *E. coli* strain DH5α was transformed with the ligated DNA by electroporation and cultured on LB solid medium [yeast extract 5 g/L; bactotryptone 10 g/L; sodium chloride 10 g/L; bactoagar 1.7%; pH 7.0] containing antibiotics, 50 mg/L of carbenicillin and 5 mg/L of gentamycin. Next, single colonies were collected. Single colonies were cultivated on LB media containing the same antibiotics to isolate plasmids from the grown strains. The size of each plasmid was primarily identified and double digested with EcoR I and Hind III to isolate a 2.8 kb DNA fragment. The resulting DNA fragments were identified to thereby complete construction of a recombinant plasmid pGmPPC (10.7 kb) containing the ppc gene.

EXAMPLE 2

Chromosomal DNA Integration Vector with Threonine Operon and ppc Gene

Figure 2:
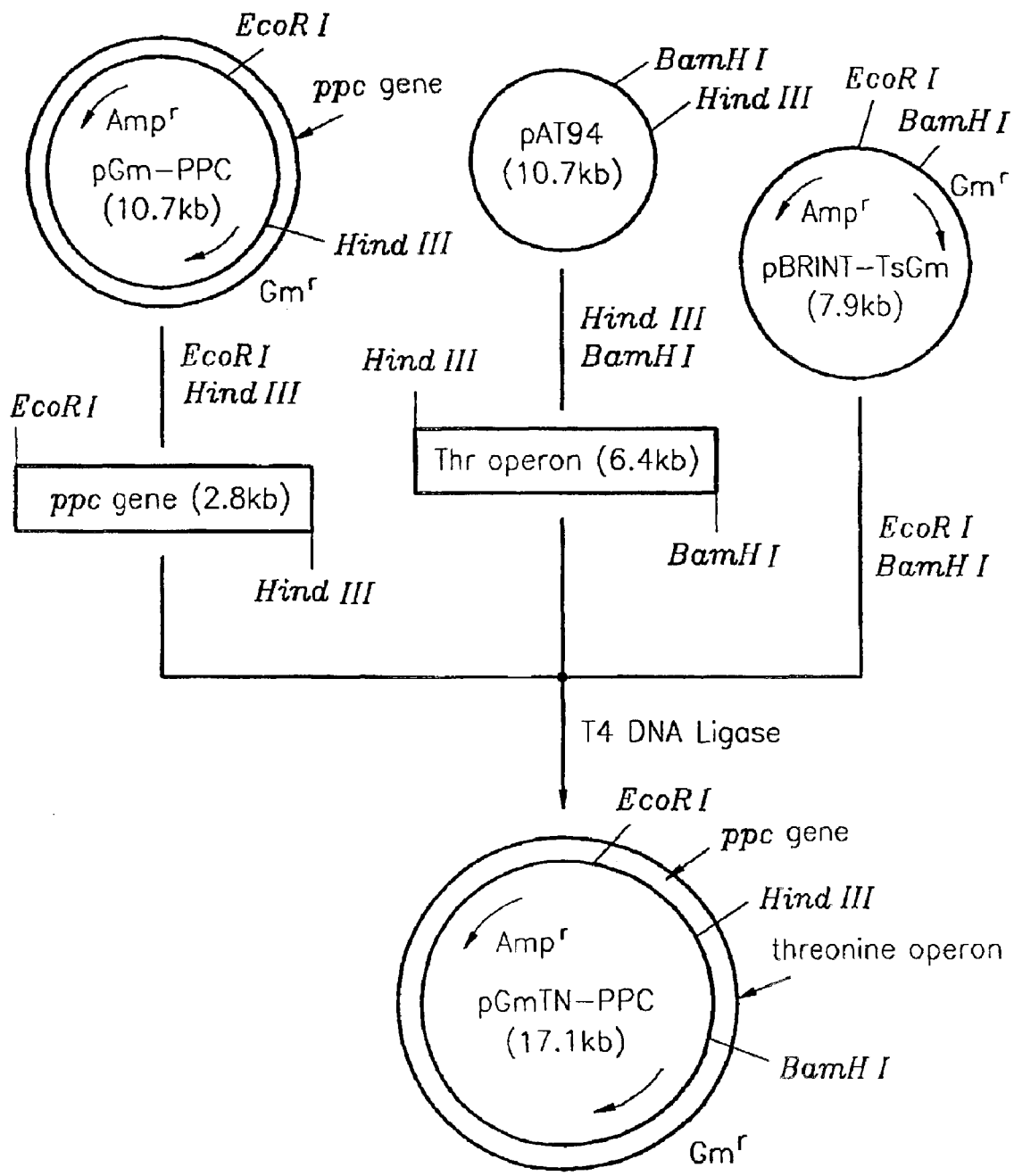
FIG. 2 depicts the construction of a recombinant plasmid pGmTN-PPC cloned with the ppc gene and the threonine operon.

Recombinant plasmid vector pAT94 (Korean Patent Application No. 92-24732) constructed by cloning with the chromosomal DNA of TF4076, was used for the threonine operon, and recombinant plasmid pGmPPC from Example 1 was used for the ppc gene. pBRINT-TsGm, a kind of pBRINT-Ts vectors, from the National University of Mexico was used as a chromosomal DNA integration vector (*Sylvie Le Beatriz et al., 1998, pBRINT-Ts: A plasmid family with a temperature-sensitive replicon, designed for chromosomal integration into the lacZ gene of Escherichia coli., Gene.,* 223, pp. 213–219). A process of construction of a recombinant plasmid is illustrated in FIG. 2. pAT94 was double digested with restriction enzymes Hind III and BamH I, and 6.4 kb threonine operon DNA fragments were isolated from the double digest by electrophoresis. pGmPPC was double digested with Hind III and EcoR I to isolate 2.8 kb ppc gene fragments. pBRINT-TsGm plasmid vector was digested with EcoR I and BamH I, and completely digested DNA fragments were isolated by the same method. The resulting plasmid vector digest, isolated threonine operon DNA fragments, and ppc gene fragments were mixed and ligated by T4 DNA ligase. *E. coli* strain DH5α was transformed with the ligated product by electroporation and cultured on LB solid medium [yeast extract 5 g/L; bactotryptone 10 g/L; sodium chloride 10 g/L; bactoagar 1.7%; pH 7.0] containing antibiotics, 50 mg/L of carbenicillin and 5 mg/L of gentamycin. Next, single colonies were collected. Single colonies were cultivated on LB media containing the same antibiotics to isolate plasmids from the grown strains. The size of each plasmid was primarily identified and double digested with EcoR I and BamH I to isolate 9.2 kb and 7.9 kb DNA fragments. The resulting DNA fragments were identified to thereby complete construction of a recombinant plasmid pGmTN-PPC (17.1 kb) containing the threonine operon and ppc gene.

EXAMPLE 3

Screen of Strain Integrated with Chromosomal Recombinant-plasmid

TF4076, a threonine producing strain, was transformed with the recombimant plasmid pGmTN-PPC isolated from *E. coli* strain DH5α, cultured on LB solid medium [yeast extract 5 g/L; bactotryptone 10 g/L; sodium chloride 10 g/L; bactoagar 1.7%; pH 7.0] containing 5 mg/L of gentamycin, and cultivated for 60 hours at 30° C. Each single colony was inoculated into 0.5 mL of LB and incubated for 4 hours at 30° C. An aliquot of the culture was transferred into 10 mL of LB, incubated for 6 hours at 30° C. and then overnight at 37° C. A $10^{-3}$–$10^{-6}$ dilution of the culture was inoculated on LB solid medium containing 5 mg/L of gentamycin. At this time, 12 μL of IPTG (0.1M) and 60 μL of X-gal (2%) were also inoculated on the LB solid medium. After 24-hour incubation at 44° C., recombinant strains were screened for white colonies sensitive to carbenicillin, which cannot grow on the LB solid medium containing 15 mg/L of carbenicillin. The screened recombinant stains confirmed the presence of the expected plasmids, in which the ppc gene and threonine operon were integrated into the lacZ gene site of the chromosomal DNA of each strain.

EXAMPLE 4

Comparison of Threonine Productivity in Flask Cultivation for Recombinant Strains Thirty single colonies of the recombinant strains with recombinant plasmids integrated into their chromosome were screened for threonine productivity comparisons using threonine titer media in Erlenmeyer flasks. The composition of the threonine titer medium used in each case is shown in Table 1. Colonies were cultured on LB solid media overnight in a 32° C. incubator. 20 mL of the titer medium was inoculated with a loopful of each culture and incubated at 32° C., 250 rpm for 48 hours. The results of the analysis are shown in Table 2. All thirty colonies of recombinant strains show excellent productivity, including eight colonies that produced 26 g/L or greater threonine, compared to the host strain, TF 3076, which produced 20 g/L of threonine. The recombinant strain, which recorded the highest threonine productivity at 27 g/L with a 35% higher yield than the host strain, was named "pGmTN-PPC12". The strain pGmTN-PPC12 was deposited Jan. 5, 2001 with the Korean Collection for Type Cultures (KCTC) and was given Accession Number KCCM 10236.

TABLE 1

Composition of Threonine Titer Medium

| Component | Amount per liter |
| --- | --- |
| Glucose | 70 g |
| $(NH_4)_2SO_4$ | 28 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| Calcium carbonate | 30 g |
| L-methionine | 0.15 g |
| Yeast extract | 2 g |
| PH 7.0 | |

TABLE 2

Results of Flask Titer Test for Recombinant Strains

| L-threonine Concentration | 20–22 g/L | 22–24 g/L | 24–26 g/L | 26 g/L or greater |
|---|---|---|---|---|
| Colony Counts | 7 | 6 | 9 | 8 |

EXAMPLE 5

Comparison of Threonine Productivity Using Fermentor

Threonine productivity in a fermentor was compared between recombinant strain pGmTN-PPC12 selected from its highest threonine titer from Example 4 and host strain TF4076. The initial medium composition used is shown in Table 3. LB media further containing per liter 10 g of glucose and 0.1 g of L-methionine were used for seed culture, and an initial volume of inoculation into a fermentor was determined at 3–5% by volume of a target initial culture. Glucose was added at a final concentration of 5% by weight each time, over 6 times in total, along with $KH_2PO_4$ at 1% by weight. Here, each addition of glucose was determined by deletion of glucose. The initial volume of the culture was 1.5 L and the final volume of the culture was 3.0 L. A total concentration of glucose added through fermentation was 250 g/L. During fermentations, the medium was stirred at 700–1000 rpm, temperature was controlled at 32° C., and pH was adjusted at 7.0 with 25–28% ammonia water. Air-flow velocity was adjusted at 0.1 vvm. The results are shown in Table 4. As shown in Table 4, the host strain TF4076 produces 75.3 g/L of threonine with a yield of 30.1% with respect to glucose consumption. In contrast, recombinant strain pGmTN-PPC12 produces 102 g/L threonine with a yield of 40.8%, which is 35.4% higher than the host strain TF4076. In addition, a similar fermentation pattern as the host strain was observed on the recombinant strain, without reduction in sugar consumption during fermentation, which often appears on recombinant strains due to growth inhibition.

TABLE 3

Initial Medium Composition in 5-L Fermentor

| Component | Amount per liter |
|---|---|
| Glucose | 50 g |
| $KH_2PO_4$ | 4 g |
| $(NH_4)_2SO_4$ | 6 g |
| Yeast extract | 3 g |
| $MgSO_4 \cdot 7H_2O$ | 2 g |
| L-methionine | 1 g |
| $FeSO_4 \cdot 7H_2O$ | 40 mg |
| $MnSO_4 \cdot 8H_2O$ | 10 mg |
| $CaCl_2 \cdot 2H_2O$ | 40 mg |
| $CoCl_2 \cdot 6H_2O$ | 4 mg |
| $H_3BO_3$ | 5 mg |
| $Na_2MoO_4 \cdot 2H_2O$ | 2 mg |
| $ZnSO_4 \cdot 7H_2O$ | 2 mg |
| PH 7.0 | |

TABLE 4

Results of Fermentative Production of Threonine by Recombinant Strains

| Strain | Threonine (g/L) | Fermentation Time (hr) | Yield (%) |
|---|---|---|---|
| TF4076 | 75.3 | 78 | 30.1 |
| pGmTN-PPC12 | 102 | 77 | 38.0 |

As described above, according to the present invention, two or more ppc genes and threonine operons are included in the chromosomal DNA to thereby enhance the expression of the ppc gene, which encodes an enzyme to convert phosphoenolpyruvate to a threonine biosynthesis precursor, oxaloacetete, and the genes encoding enzymes involved in the synthetic pathway of threonine from oxaloacetate, including thrA (aspartokinasel-homoserine dehydrogenase), thrB (homoserine kinase), and thrC (threonine synthase). The present invention can remarkably improve productivity of L-threonine by 35% higher than the host strain.

What is claimed is:

1. An isolated *Escherichia coli* strain pGmTN-PPC 12 of Accession No. KCCM 10236 capable of L-threonine production.

2. A method for producing L-threonine comprising: culturing the *Escherichia coli* strain pGmTN-PPC12 (Accession No. KCCM 10236) of claim 1 with substrates to produce L-threonine; and isolating the produced L-threonine.

* * * * *